(12) United States Patent
Schatz et al.

(10) Patent No.: US 8,367,392 B2
(45) Date of Patent: Feb. 5, 2013

(54) GENETIC TRANSFORMATION OF ALGAL AND CYANOBACTERIA CELLS BY MICROPORATION

(75) Inventors: Daniella Schatz, Rehovot (IL); Doron Eisenstadt, Haifa (IL); Jonathan Gressel, Rehovot (IL); Shai Ufaz, Givat Ada (IL); Ofra Chen, Rehovot (IL); Dikla Journo Eckstein, Even-Shmuel (IL)

(73) Assignee: Transalgae Ltd., Rehovot (IL)

( * ) Notice: Subject to any disclaimer, the term of this patent is extended or adjusted under 35 U.S.C. 154(b) by 575 days.

(21) Appl. No.: 12/584,571

(22) Filed: Sep. 8, 2009

(65) Prior Publication Data

US 2010/0081177 A1    Apr. 1, 2010

Related U.S. Application Data

(60) Provisional application No. 61/191,169, filed on Sep. 5, 2008, provisional application No. 61/191,453, filed on Sep. 9, 2008.

(51) Int. Cl.
*C12N 1/12* (2006.01)
*C12N 1/20* (2006.01)

(52) U.S. Cl. .................................. 435/252.2; 435/252.1

(58) Field of Classification Search .................. 800/292, 800/296; 435/257.1–257.6, 252.1–251.3
See application file for complete search history.

(56) References Cited

U.S. PATENT DOCUMENTS

| | | |
|---|---|---|
| 3,431,200 A | 3/1969 | Davis et al. |
| 3,521,400 A | 7/1970 | Ort et al. |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,680,314 A | 7/1987 | Nonomura |
| 4,683,202 A | 7/1987 | Mullis |
| 4,801,531 A | 1/1989 | Frossard |
| 4,879,219 A | 11/1989 | Wands |
| 4,945,050 A | 7/1990 | Sanford |
| 5,011,771 A | 4/1991 | Bellet |
| 5,192,659 A | 3/1993 | Simons |
| 5,272,057 A | 12/1993 | Smulson |
| 5,281,521 A | 1/1994 | Trojanowski |
| 5,451,514 A | 9/1995 | Boudet et al. |
| 5,512,466 A | 4/1996 | Klee et al. |
| 5,661,017 A | 8/1997 | Dunahay |
| 5,723,765 A | 3/1998 | Oliver et al. |
| 5,731,180 A | 3/1998 | Dietrich |
| 5,804,408 A | 9/1998 | Hagiwara |
| 5,910,626 A | 6/1999 | Haselkorn |
| 5,948,956 A | 9/1999 | Lee et al. |
| 6,114,603 A | 9/2000 | Christou et al. |
| 6,198,024 B1 | 3/2001 | Yanofsky et al. |
| 6,720,174 B1 | 4/2004 | Lehmann |
| 6,849,776 B1 | 2/2005 | Kuvshinov |
| 6,855,365 B2 | 2/2005 | Short |
| 7,211,431 B2 | 5/2007 | Rao et al. |
| 7,285,701 B2 | 10/2007 | Kakefuda |
| 7,410,637 B2 | 8/2008 | Sayre et al. |
| 7,745,696 B2 | 6/2010 | Melis et al. |
| 2002/0009479 A1 | 1/2002 | Vardi |
| 2003/0097678 A1 | 5/2003 | Kushinov et al. |
| 2004/0172678 A1 | 9/2004 | Gressel et al. |
| 2005/0260758 A1 | 11/2005 | Rasochova et al. |
| 2005/0266541 A1 | 12/2005 | Dillon |
| 2006/0143730 A1 | 6/2006 | Kakefuda |
| 2007/0050863 A1 | 3/2007 | Tranel |
| 2007/0074303 A1 | 3/2007 | McCutchen |
| 2007/0130654 A1 | 6/2007 | Thomas |
| 2007/0148166 A1 | 6/2007 | Wu et al. |
| 2007/0178451 A1 | 8/2007 | Deng |
| 2007/0178452 A1 | 8/2007 | Bouffard et al. |
| 2008/0099405 A1 | 5/2008 | Polak et al. |
| 2008/0120749 A1 | 5/2008 | Melis et al. |
| 2008/0128331 A1 | 6/2008 | Lean |
| 2008/0160591 A1 | 7/2008 | Willson et al. |
| 2008/0176304 A1 | 7/2008 | Lee |
| 2008/0206840 A1 | 8/2008 | Gerdes et al. |
| 2009/0050538 A1 | 2/2009 | Lean |
| 2009/0114601 A1 | 5/2009 | Lean |

(Continued)

FOREIGN PATENT DOCUMENTS

| | | |
|---|---|---|
| WO | WO 96/34088 | 10/1996 |
| WO | WO 97/29123 | 8/1997 |

(Continued)

OTHER PUBLICATIONS

Thiel, T., et al. J. Bacteriol. Oct. 1989; pp. 5743-5746.*
(http://phototroph.blogspot.com/2006/11/pigments-and-absorption-spectra.html) Oct. 26, 2006.
Adams, E et al; (1998); Impacts of reducedpH from ocean CO2 disposal: Sensitivity of zooplankton mortality to model parameters; Waste Management; 17 (5-6): 375-380.
Al-Ahmad, et al; (2004); Tandem constructs to mitigate transgene persistence: tobacco as a model; Molecular Ecology; 13:697-710.
Al-Kaff et al. Transcriptional and Posttranscriptional Plant Gene Silencing in Response to a Pathogen, Science, 1998, vol. 279,pp. 2113-2115.

(Continued)

*Primary Examiner* — Russell Kallis
(74) *Attorney, Agent, or Firm* — Graeser Associates International Inc; Dvorah Graeser

(57) ABSTRACT

A method for transforming algal or cyanobacterial cells, comprising mixing a polynucleotide for transforming the cells with the polynucleotide; performing microporation by applying a plurality of electrical pulses to the cells with a microporation apparatus; and incubating said polynucleotide with the cells after said applying said electrical pulses.

7 Claims, 2 Drawing Sheets

U.S. PATENT DOCUMENTS

Figure 1:
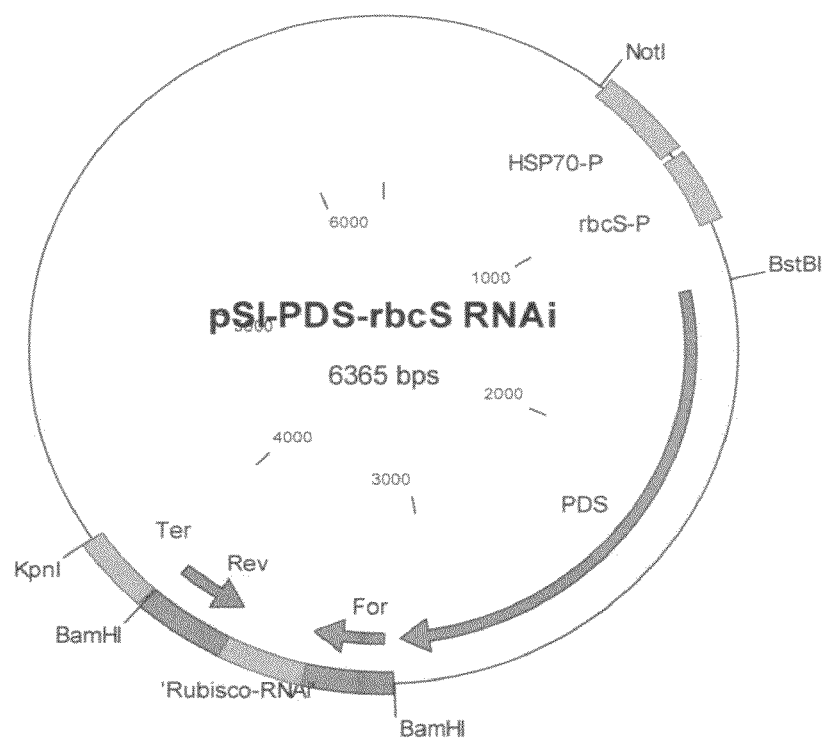

| | | | |
|---|---|---|---|
| 2009/0181438 | A1 | 7/2009 | Sayre |
| 2009/0215179 | A1 | 8/2009 | Gressel et al. |
| 2010/0068816 | A1 | 3/2010 | Chen et al. |
| 2010/0081177 | A1 | 4/2010 | Schatz et al. |

FOREIGN PATENT DOCUMENTS

| | | |
|---|---|---|
| WO | WO 97/30162 | 8/1997 |
| WO | WO 97/42326 | 11/1997 |
| WO | WO 2004/007691 | 1/2004 |
| WO | WO 2004/046362 | 6/2004 |
| WO | WO 2005/072254 | 8/2005 |
| WO | WO 2010/027505 | 3/2010 |

OTHER PUBLICATIONS

Altenbach et al; (1989); Enhancement of the methionine content of seed proteins by the expression of a chimeric gene encoding a methionine-rich protein in transgenic plants; Plant Molecular Biology; 13: 513-522.

Ufaz et al: 'Improving the content of essential amino acids in crop plants: Goals and Opportunities.' Plant Physiology vol. 147, 2008, pp. 954-961.

Azpiroz et al., An Arabidopsis Brassinosteroid-Dependent Mutant is Blocked in Cell Elongation. The Plant Cell, 1998 American Society of Plant Biologists, US. vol. 10,pp. 219-230.

Bally, J. et al.: 'Plant Physiological Adaptations to the Massive Foreign Protein Synthesis Occurring in Recombinant Chloroplasts' Plant Physiology vol. 150, Jul. 2009, pp. 1474-1481.

Bartsch, et al; (2001); Biosafety of hybrids between transgenic virus-resistant sugar beet and Swiss chard; Ecoclogical Applications; 11(1): 142-147.

PCT/IL00/000046 International Search Report—Jun. 9, 2000.

PCT/US10/000918 International Search Report—May 14, 2010.

Borkhsenious, O.N. et al.: 'The Intracellular Localization of Ribulose-1,5-Bisphosphate Carboxylase/Oxygenase in Chlamydomonas reinhardtii' Plant Physiol. vol. 116, 1998, pp. 1585-1591.

Carpenter.: 'Phosphorus control is critcal to mitigating eutrophicatio' Proc Natl Acad Sci USA. vol. 105, No. 32, Aug. 12, 2008, pp. 11039-11040.

Colarado State Website; (2002); Crop-to-weed gene flow; Transgenic Crops: An Introduction and Resource Guide.

Colliver, et al; (1997); Differential modification of flavonoid and isoflavonoid biosynthesis with an antisense chalcone synthase construct in transgenic Lotus corniculatus; Plant Molecular Biology; 35: 509-522.

Crawley et al., Ecology of Transgenic Oilseed Rape in Natural Habitats. Nature: international weekly journal of science, 1993. Vol. 363,pp. 620-623.

Daniell, et al; (1998); Containment of herbicide resistance through genetic engineering of the chloroplast genome; Nature Biotechnology; 16:345-348.

Dasgupta et al., Co-Ordinated Expression of Multiple Enzymes in Different Subcellular Compartments in Plants, The Plant Journal, 1998 Blackwell Scientific Publications, Oxford, GB, vol. 16,Nr:1,pp. 107-116.

Dasplanque, et al; (2002); Transgenic weed beets: possible, probable, avoidable?; Journal of applied Ecoclogy; 39(4): 561-571.

Database Genbank [Online] Aug. 1, 2002 '1030009G10.y2 C. reinhardtii CC-1690, Deflagellation (normalized), Lambda Zap II Chlamydomonas reinhardtii cDNA, mRNA sequence' Database accession No. BQ809195.

Database Genbank [Online] Nov. 14, 2006 'Chlamydomonas reinhardtii nuclear gene rbcS2 for ribulose bisphophate carboxylase/oxygenase small subunit (EC 4.1.1.39).' Database accession No. X04472.1.

Deng M. D. and J.R. Coleman (1999). "Ethanol synthesis by genetic engineering in cyanobacteria." Appl Environ Microbiol 65(2):523-8.

PCT/US09/000033 International Search Report—Mar. 9, 2009.

Fuhrmann et al; (1999); A synthetic gene coding for the green fluorescent protein (GFP) is a versatile reporter in Chlamydomonas reinhardtii; The Plant Journal; 19(3): 353-361.

Golden S. S., J. Brusslan et al.(1987) "Genetic engineering of the cyanobacterial chromosome." Methods Enzymol 153: 215-31.

Goldman, et al; (1994); Molecular markers associated with maize kernel oil concentration in an Illinois high protein×Illinois low protein cross; Crop Science; 34:908-915.

Gressel, J. and A. A. Levy (2006) Agriculture—the selector of improbable mutations. Proceedings of the National Academy of sciences USA 103: 12215-12216.

Gressel, et al; (2000); Genetic and Ecological Risks from Biotechnologically—Derived Herbicide—Resistant Crops: Decision Trees for Risk Assessment; Plant Breeding Reviews; 18(5): 251-303.

Gressel, et al; (2000); Introgressional Failsafes for Transgenic Crops; Xieme Colloque International sur la Biologie des Mauvais Herbes; 8 P.

Gressel, et al; (2003); Containment and mitigation of transgene flow from crops; The BCPC International Congress—Crop Science and Technology; 1175-1180.

Gressel, J; (1999); Tandem Constructs: Preventing the Rise of Superweeds ; Tibtech; 17:361-366.

Gressel, J; (2001); Potential failsafe mechanisms against the spread and introgression of transgenic hypervirulent biocontrol fungi; Trends in Biotechnology; 19(4): 149-154.

PCT/US09/005034 International Search Report—Mar. 25, 2010.

Gressel, J; (2008); 'Transgenics are imperative for biofuel crops.' Plant Sci.; 174(3): 246-263.

Grzebyk D., O. Schofield, P. Falkowski and J. Bernhard (2003) The Mesozic radiation of eukaryotic algae: the portable plasid hypothesis. J. Phycol. 39:259-267).

Gudin and Chaumont et al; (1980); A biotechnology of photosynthetic cells based on the use of solar energy; Biochem Soc Trans; 8(4): 481-2.

Hunter, W; (2002); Bioremediation of chlorate or perchlorate contaminated water using permeable barriers containing vegetable oil; Current Microbiology; 45: 287-292.

Jorgensen et al., Spontaneous Hybridization Between Oilseed Rape (Brassica napus) Andweedy B. Campestris (Brassicaceae): A Risk of Growing Genetically Modified Oilseed Rape. American Journal of Botany, 1994. vol. 81,Nr:12,pp. 1620-1626.

PCT/US2009/005067 International Search Report—Apr. 2, 2010.

Kindle, K L. (1990) "High-frequency nuclear transformation of Chlamydomonas reinhardtii." Proc. Natl. Acad. Sci. USA 87:1228-1232.

PCT/US2010/002632 International Search Report—Nov. 18, 2010.

Knuckey et al.: 'Production of microalgal concentrates by flocculation and their assessment as aquaculture feeds' Aquacultural Engineering vol. 35, No. ISS.3, Oct. 2006, pp. 300-313.

Koltunow et al., Apomixis: Molecular Strategies for the Generation of Genetically Identical Seeds Without Fertilization . Plant Physiology, 1995. vol. 108,pp. 1345-1352.

Kurihara H., A. Ishimatsu, et al. (2004) "Effects of elevated seawater CO2 concentration on the meiofauna." Journal of Marine Science and Technology: 17-22.

Kushinov, et al; (2001); Molecular control of transgene escape from genetically modified plants; Plant Science; 160: 517-522 {Abstract Only}.

Kushinov, et al; (2004); Barnase gene inserted in the intron of GUS—a model for controlling transgene flow in host plants; Plant Science; 167: 173-182.

Landbo, et al; (1997); Seed germination in weedy Brassica campestris and its hybrids with B. napus: Implications for risk assessment of transgenic oilseed rape; Euphytica; 97(2): 209-216.

Lermontova, I., Kruse E., Mock, H. P. & Grimm, B. (1997). "Cloning and characterization of a plastidal and a mitochondrial isoform of tobacco protoporphyrinogen IX oxidase." Proc. Natl. Acad. Sci. USA 94,8895-8900.

Li et al. (2008); 'Transgenic microalgae as a non-antibiotic bactericide producer to defend against bacterial pathogen infection in the fish digestive tract' Fish & Shellfish Immunology, 26(2): 316-325.

Li et al; (2000); A pigment-binding protein essential for regulation of photosynthetic light harvesting; Nature; 403:391-395.

Linder, C; (1998); Potential persistence of transgenes: seed performance of transgenic canola and wildx canola hybrids; Ecoclogical Applications; 8(4): 1180-1195.

Lioudmila, A., Zaslavskaia, et al. (2000). "Transformation of the diatom phaeodactylum tricomutum (Bacillariophyceae) with a variety of selectable marker and reporter genes" J. Phycol. 36, 379-386.

Makino, A. et al.: 'Does Decrease in Ribulose-I ,5-Bisphosphate Carboxylase by Antisense RbcS Lead to a Higher N-Use Efficiency of Photosynthesis under Conditions of Saturating CO, and Light in Rice Plants?' Plant Physiol. vol. 114, 1997, pp. 483-491.

Mena et al.: 'Blue fluorescent proteins with enhanced brightness and photostability from a structurally targeted library.' Nature Biotechnology vol. 24, No. 12, 2006, pp. 1569-1571.

Young et al. Heritability of Resistance to Seed Shattering in Kleingrass. Crop Science: a journal serving the international community of crop scientists, 1991. vol. 31,pp. 1156-1158.

Michel et al.: 'Somatic mutation-mediated evolution of herbicide resistance in the nonindigenous invasive plant hydrilla (*Hydrilla verticillata*)' Molecular Ecology vol. 13, 2004, pp. 3229-3237.

Navarro et al.; (1996); Constitutive expression of nitrate reductase changes the regulation of nitrate and nitrite transporters in *Chlamydomonas reinhardtii*; The Plant Journal; 9(6): 819-827.

Oard, et al; (2000); Field evaluation of seed production, shattering, and dormancy in hybrid populations of transgenic rice (*Oryza sativa*) and the weed, red rice (*Oryza sativa*): Plant Science; 157(1): 13-22.

Paterson et al. The Weediness of Wild Plants: Molecular Analysis of Genes Influencing Dispersal and Persistence of Johnsongrass, *Sorghum halepense* (L.) Pers. Proceedings of the National Academy of Sciences of USA, 1995. vol. 92,pp. 6127-6131.

Patzoldt, W. L., Hager, A.G et al (2006). "A codom deletion confers resistance to herbicides inhibiting protoporphyrinogen oxidase." PNAS 33: 12329-12334.

Windhovel et al.: 'Expression of Erwinia uredovora Phytoene Desaturase in Synechococcus PCC7942 Leading to Resistance against a Bleaching Herbicide' Plant Physiol. vol. 104, 1994, pp. 119-125.

Zemetra et al. Potential for Gene Transfer Between Wheat (*Triticum aestivum*) and Jointed Goatgrass (*Aegilops cylindrica*). Weed Science, 1998. vol. 46,pp. 313-317.

Prokop et al; (1984); Spectral shifting by dyes to enhance algae growth; Biotechnology and Bioengineering; vol. XXVI; 1313-1322.

Quick, W.P. et al.: 'The impact of decreased Rubisco on photosynthesis, growth, allocation and storage in tobacco plants which have been transformed with antisense rbcS' Plant Journal vol. 1(1), 1991, pp. 51-58.

Reichman, et al; (2006); Establishment of transgenic herbicide-resistant creeping bentgrass (*Agrostis stolonifera* L.) in nonagronomic habitats; Molecular Ecology; 15(3): 4243-4255; Abstract Only.

Ritala, et al; (2002); Measuring gene flow in the cultivation of transgenic barley; Crop Science; 42:278-285 {Abstract Only}.

Rohr et al.; (2004); Tandem reverted repeat system for selection of effective transgenic RNAi strains in Chlamydomonas; The Plant Journal; 40:611-621.

Schaller et al. Overexpression of an Arabidopsis cDNA encoding a sterol-C24(1)-methyltransferase in tobacco modifies the ratio of 24-methyl cholesterol to sitosterol and is associated with growth reduction. Plant Physiol, 1998. vol. 118,Nr:2,pp. 461-469.

Sheehan J., T. Dunahay, et el. (2004) A look back at the US Department of Energy's Aquatic species Program: Biodiesel from Algae; Close-Out Report, Island Press.

Sizova I., Fuhrmann, M., et al. (2001). A streponyces rimosus aphVIII gene coding for a new type phosphotransferase provides stable antibiotic resistansce to Chla,ydomonas reinhardtii. Gene 277:221-229.

Snow et al. Fecundity, Phenology, and Seed Dormancy of F1 Wild-Crop Hybrids in Sunflower (*Helianthus annuus*, Asteraceae). American Journal of Botany, 1998. vol. 85,Nr:6,pp. 794-801.

Williams et al. Genetic Engineering for Pollination Control. Transgenics, 1995. vol. 13,pp. 344-349.

Stevens, et al. (1994); Isolation and characterization of five genotypic mutants of chlorat-resistant Cyanobacteria Unable to utilise Nitrate; Current Microbiology; 29:311-318.

Takahashi et al; (1999); Genetically engineered herbicide resistance in cyanobacterium; Biotechnology Letter; 21:751-757.

Veloso et al: 'Lipid Production by *Phaeodactylum tricornutum*' Bioresource Technology vol. 38, 1991, pp. 115-119.

Vleeshouwers et al., The Effect of Seed Dormancy on Percentage and Rate of Germination in *Polygonum persicaria*, and Its Relevance for Crop-Weed Interaction. Annals of Applied Biology, 1998. vol. 132,pp. 289-299.

Wang, et al; (1998); Constitutive Expression of the Circadian Clock Associated 1 (CCA1) Gene Disrupts Circadian Rhythms and Suppresses Its Own Expression: Cell; 93: 1207-1217.

Watanabe, N., Che F. S., Iwano, M., Takayama, S. & Yoshida, S (2001). "Construction of an *Amaranthus hyochondriaus* Bacterial Artificail chromosome Libaray and Genomic Sequencing of Herbicide Target Genes" J. Biol. chem. 276, 20474-20481.

.'Wikipedia, RuBisCO', [Online] Nov. 18, 2009, Retrieved from the Internet: [retrieved on Dec. 26, 2009].

Wyman et al.: 'Molecular and Physiological Responses of Two Classes of Marine Chromophytic Phytoplankton (Diatoms and Prymnesiophytes) during the Development of Nutrient-Stimulated Blooms.' Appl Environ Microbiol. vol. 66, No. 6, 2000, pp. 2349-2357.

Divakaran, R and V.N.S. Pillai (2002) Flocculation of algae using chitosan. J. Appl. I Phycology 14:419-422.

Franklin SE and Mayfield SP. (2004) Prospects for molecular farming in the green alga *Chlamydomonas reinhardtii*. Curr Opin Plant Biol, 7: 159-165.

Huntley M.E. and Redalje, D.G. (2007). $CO_2$ mitigation and renewable oil from photosynthetic microbes: A new appraisal, Mitig. Adapt. Strateg. Glob. Change 12, 573-608.

Leentvar, J ., Rebhun, M., 1982. Effect of magnesium and calcium precipitation on coagulation—flocculation with lime. Water Res. 16, 655-662.

Liu X, and Gorovsky MA (1993) Mapping the 5' and 3' ends of *Tetrahymena thermophila* mRNAs using RNA ligase mediated amplification of cDNA ends (RLM-RACE). Nucl Acids Res 21: 4954-4960.

Schroda M. (2006) RNA silencing in Chlamydomonas: mechanisms and tools. Curr Genet 49: 69-84.

Takahashi, M.Goldschmidt-Clermont, S.-Y.Soen, L.G.Franzen1 and J.- . D.Rochaix. (1991) Directed chloroplast transformation in *Chlamydomonas reinhardtii*: insertional inactivation of the psaC gene encoding the iron sulfur protein destabilizes photosystem I. EMBO J . 10: 2033-2040.

Alfafara C.G. et al (2002) Operating and scale-up factors for the electrolytic removal of algae from eutrophied lake water. Journal of Chemical Technology & Biotechnology 77: 8 871-876.

Avnimelech Y. et al (1982) Mutual flocculation of algae and clay: evidence and implications. Science 216, 63-65.

Bilanovic D. et al (1988) Flocculation of microalgae with cationic polymers: effects of medium salinity. Biomass 17, 65-76.

Blake M.S. et al (1984) A rapid, sensitive method for detection of alkaline phosphatase-conjugated anti-antibody on Western blots. Anal Biochem l36:175-9.

Blanchemain A. et al (1999) Increased production of eicosapentaenoic acid by *Skeletonema costatum* cells after decantation at low temperature. Biotechnology Techniques 13: 497-501.

Dziubek A.M. et al (1989) High-pH coagulation-adsorption: a new technology for water treatment and reuse. Water Sci. Technol. 21, 51 1-517. 1962.

Eijlander et al. Biological Containment of Potato (*Solanum tuberosum*): Outcrossing to the Related Wild Species Black Nightshade (*Solanum nigrum*) and Bittersweet, Jul. 6, 1993.

Elmaleh S. et al (1996) Suspended solids abatement by pH. Increase—upgrading of an oxidation pond effluent.Wat. Res. 30: 2357-2362.

Folkman Y. et al (1973) Removal of algae from stabilization pond effluents by lime treatment. Water Research 7: 419-435.

Heiman Y. et al (2003) Genes encoding A-type flavoproteins are essential for photoreduction of O2 in cyanobacteria. Curr Biol 13: 230-235.

Henderson R. K. et al (2008b) The impact of algal properties and pre-oxidation on solid-liquid separation of algae. Water Res. 42:1 827-1845.

Henderson R. K. et al (2008a) Successful removal of algae through control of the zeta potential. Separation Sci. Tech.43: 1653-1666.

Henderson R. K. et al (2008c) Surfactants as bubble surface modifiers in the flotation of algae: dissolved air flotation that utilizes a chemically modified bubble surface, Environ. Sci. Technol., 42: 4883-4888.

Kang R. J. et al (2005) 'Effects of co-expression of two higher plants genes ALD and TPI in *Anabaena* sp. PCC7120 on photosynthetic CO2 fixation' Enzyme and Microbialtechnology vol. 36, pp. 600-604.

Lavoie A. et al (1983). Harvesting microalgae with chitosan. J. World Mariculture Soc., 14, 685 94.

Lee S. J. et al (1996) Effects of harvesting method and growth stage on the flocculation of the green alga *Botryococcus braunii*. Letters in Applied Microbiology 27: 14-18.

Levin G. V. et al (1962) Harvesting of algae by froth flotation. Appl. Microbiol. 10: 169-175.

Lumbreras V. et al (1998) Efficient foreign gene expression in *Chlamydomonas reinhardtii* mediated by an endogenous intron. Plant J 14: 441-447.

Ma, VM. et al (2007) Increased activity of the non-regulated enzymes ructose-1,6-bisphosphate aldolase and triosephosphate isomerase in *Anabaena* sp strain PCC 7120 increases photosynthetic yield, J Appl Phycol 19:207-213.

McCausland M. A. et al (1999) Evaluation of live microalgae and microbial pastes as supplementary food for Pacific oysters. Aquaculture 174:323-342.

Millamena, O. M. et al (1991) Techniques on algae harvesting and preservation for use in culture and a larval food. Aquacultural Eng. 9:295-304.

Morales, J. et al (1985) Harvesting marine microalgae species by chitosan flocculation. Aqua. Engng, 4, 257-70.

Murakami M. et al (1997) The biological CO2 fixation and utilization project by RITE (2)—Screening and breeding of microalgae with high capability in fixing CO2. Energy Convers Mgmt. 38: S493-S497.

Negoro M. et al (1993) Carbon dioxide fixation by microalgae photosynthesis using actual flue gas discharged from a boiler, 39: 643-653.

Paul J. H. et al (2000) Diel Patterns of Regulation of rbcL Transcription in a Cyanobacterium and a Prymnesiophyte Mar. Biotechnol. vol. 2, pp. 429-436.

Prentki P. et al (1984) In vitro insertional mutagenesis with a selectable DNA fragment. Gene 29: 303-313.

Semerjian, L. et al (2003) High-pH-magnesium coagulation-flocculation in wastewater treatment Advances in Environmental Research 7: 389-403.

Stanier R. Y. et al (1971) Purification and properties of unicellular blue-green algae (order Chroococcales). Bacteriol. Q Rev. 35: 171-205.

Sukenik A et al (1984) Algal autoflocculation—verification and proposed mechanism. Biotechnology and Bioengineering, 26: 142-147.

Wyman M. et al (1985) Novel role for phycoerythrin in a marine cyanobacterium, Synechochoccus strain DC2. Science 230: 818-820.

Yahi, H. (1994) Algal flocculation-sedimentation by pH increase in a continuous reactor. Water science & technology 30: 259-267.

Zhang, G. et al (2006) Removal of algae by sonication-coagulation. Journal of Environmental Science and Health Part A, 41:1379-1 390.

Soria G. et al (2009) Chemokines in Human Breast Tumor Cells: Modifying Their Expression Levels and Determining Their Effects on the Malignancy Phenotype. Methods in Enzymology, vol. 460.

Wang Y. et al (2008) Microporation Is a Valuable Transfection Method for Gene Expression in Human Adipose Tissue-derived Stem Cells. Published online Dec. 9, 2008. doi:10.1038/mt.2008.267.

Lefebvre B. et al (2010) Efficient gene delivery and silencing of mouse and human pancreatic islets. BMC Biotechnology 2010.

MicroPorator MP-100, User's Manual (2008) MP-100 Rev.M.03.52-06/08.

Young, B; (1991); Heritability of Resistance to Seed Shattering in Kleingrass; Crop Sci. 31: 1156-1158 (Abstract).

* cited by examiner

GENETIC TRANSFORMATION OF ALGAL AND CYANOBACTERIA CELLS BY MICROPORATION

PRIORITY

This application claims priority of the U.S. Provisional application Nos. 61/191,169 filed on Sep. 5, 2008 and 61/191,453 filed on Sep. 9, 2008.

SEQUENCE LISTING

This application contains sequence data provided on a computer readable diskette and as a paper version. The paper version of the sequence data is identical to the data provided on the diskette

FIELD OF THE INVENTION

This invention relates to the field of genetically engineering algae and cyanobacteria to grow more efficiently on industrial waste emissions of carbon dioxide and is applicable for use with algae and cyanobacteria cultured in closed bioreactors and covered or open ponds for producing high value products, as well as biofuels. It builds on integrating principles of genetic engineering, photosynthetic physiology and biochemistry, chemical engineering of bioreactors, and waste emission engineering.

BACKGROUND OF THE INVENTION

A major breakthrough in the large scale cultivation of algae and cyanobacteria to produce commercially useful products was the discovery that many such species could be cultivated with flue gas (up to 80% $CO_2$) or even pure $CO_2$ whereas most other organisms (plants and animals) are "biochemically anaesthetized" at $CO_2$ levels of 5% or higher, slowing all metabolism. This opened the way for cultivating such organisms on $CO_2$ emissions to the environment (Murakami and Ikenouchi 1997, Negoro, et al. 1993).

Cyanobacteria have already begun to be genetically engineered to utilize these elevated $CO_2$ levels by over expressing genes encoding rate limiting enzymes of the "dark reactions" ($CO_2$ assimilating reactions that utilize NADPH and ATP from the light reactions) of photosynthesis. Thus, for example, engineering genes from rice encoding for cytosolic fructose-1,6-bisphosphate aldolase and spinach triose phosphate isomerase in cells of a cyanobacterium doubled their activities and greatly increased photosynthetic efficiency and biomass yields (Kang et al. 2005, Ma et al. 2007).

However, one can only over-express enzymes to a limited extent, as the cell does not have unlimited capacity. Therefore, the existing methods have only a limited capacity and there is a need to improve these methods to enhance the use of elevated carbon dioxide concentration in algal cultures.

SUMMARY OF THE INVENTION

The instant invention provides a solution to this existing problem by reducing the levels of other enzymes to "make room" for the over expressed, rate limiting enzymes such as fructose-1,6-bisphosphate aldolase (ALD), chloroplast triosephosphate isomerase (TPI) or acetyl CoA carboxylase (ACCase) that enhance sink capacity to utilize fixed carbon dioxide.

Ribulose-1,5-bisphosphate carboxylase/oxygenase (RUBISCO) is the key photosynthetic enzyme that catalyzes the first step of $CO_2$ fixation. The chloroplast localized holoenzyme of plants and algae in Sub-kingdom Viridaeplantae, Phylum Chlorophyta (heretofore referred to as green algae) contain eight nuclear genome encoded small subunits and eight chloroplast genome encoded large subunits. In red lineage algae (Sub-Kingdom Chromobiota, Phylum Haptophyta, Heterokonotophyta, Bacillariophyta and others (Table 1), all sub-units are encoded in the chloroplast.

TABLE 1

Phylogeny of some of algae used

| Genus | Family | Order | Phylum | Sub-Kingdom |
| --- | --- | --- | --- | --- |
| *Chlamydomonas* | Chlamydomonadaceae | Volvocales | Chlorophyta | Viridaeplantae |
| *Nannochloris* | Coccomyxaceae | Chlorococcales | Chlorophyta | Viridaeplantae |
| *Tetraselmis* | Chlorodendraceae | Chlorodendrales | Chlorophyta | Viridaeplantae |
| *Phaeodactylum* | Phaeodactylaceae | Naviculales | Bacillariophyta | Chromobiota |
| *Nannochloropsis* | Monodopsidaceae | Eustigmatales | Heterokontophyta | Chromobiota |
| *Pavlova* | Pavlovaceae | Pavlovales | Haptophyta | Chromobiota |
| *Isochrysis* | Isochrysidaceae | Isochrysidales | Haptophyta | Chromobiota |

Phylogeny according to: http://www.algaebase.org/browse/taxonomy/
Note:
Many genes that in higher plants and *Chlorophyta* are encoded in the nucleus are encoded on the chloroplast genome (plastome) of Chromobiota, red lineage algae (Grzebyk, et al. (2003).

The present consensus is that even more RUBISCO is needed for efficient photosynthesis, as demonstrated in the recent suggestion that elevated RUBISCO would enhance the rate of photosynthesis in algae commercially cultivated for biofuels (Huntley and Redalje 2007). Counter-intuitively, the inventors of this disclosure chose to "make room" for other enzymes by reducing concentration of the RUBISCO enzyme, typically considered to be rate limiting for $CO_2$ assimilation in photosynthetic cells; RUBISCO can comprise up to 70% of the soluble protein in plant cells.

Photosynthesis produces the sugars needed for the biosynthesis of the specific primary and secondary metabolites of interest in each case (biofuels, pigments, enzymes, pharmaceuticals, starch, etc.). RUBISCO is the first enzyme in the dark reactions of photosynthesis, "fixing" carbon dioxide onto an organic molecule. The later reactions use NADPH and ATP generated by the light reactions to reduce the fixed $CO_2$ to carbohydrates. RUBISCO was the best enzyme evolution could produce pre-antiquity, which was of little matter early in the evolution of earth, e.g. in the Archean era 3.5 billion years ago when $CO_2$ concentrations in the atmosphere were thought to be at least 100 times more than at present (FIG. 1.4 in Falkowski and Raven, 1997), and the very low affinity for $CO_2$ to RUBISCO was of little consequence. As oxygenous photosynthesis began to remove $CO_2$ from the atmosphere and elevate atmospheric $O_2$, the levels of RUBISCO became limiting, and evolution gradually increased the levels of RUBISCO in photosynthetic organisms to the present high levels. Presently, high concentrations of $CO_2$ can be inexpensively provided to algae and cyanobacteria in culture from industrial combustion of fuels. This will lead to much of the RUBISCO being superfluous, and decreasing its content "makes way" for over-expressing other enzymes needed for photosynthesis as well as releasing resources for more soluble products. This would be one way of sequestering large amounts of carbon dioxide, presently imperative due to the purported relationships between elevated global carbon dioxide levels and global warming. Even though the small subunit of RUBISCO is encoded by a family of genes, the gene products are interchangeable, with considerable consensus among them.

According to this disclosure, reducing RUBISCO in green algae can be done by using either antisense or RNAi technology, both targeting the consensus sequences of the small nuclear encoded subunit, which, in many cases, has been shown to control the biosynthesis of both subunits. Obviously, total suppression is undesirable, as RUBISCO is needed for $CO_2$ fixation. The level of suppression that is advantageous is a function of: a. experimental determination for each pond or bioreactor condition and concentration of $CO_2$ introduced into the system; and b. the availability of the $CO_2$ to the organisms in the medium. Reducing RUBISCO in red lineage algae according to this disclosure, can be done by knockout of one or both RUBISCO subunits in the chloroplast by homologous recombination and transformation of the same RUBISCO gene under a mutated promoter, which will decrease the RUBISCO expression level.

Many algae and especially cyanobacteria have atypical (for higher organisms) G:C contents and consequently atypical codon usages and DNA sequences. While there is a high consensus in amino acid sequences in RUBISCO subunits, it is far less at the nucleotide level, requiring sequencing of the genes encoding RUBISCO subunits from each target organism before embarking on generating RNAi or antisense constructs and engineering them into the cell thus reducing RUBISCO according to the codon usage of the target organism.

One drawback to genetically engineering algae and cyanobacteria for large scale cultivation is the risk of inadvertent "spills" into the environment. It is highly unlikely (i.e. as near to impossible as a scientist can evaluate) that organisms optimized to live and grow in an atmosphere of >5% $CO_2$, yet having a lower than normal RUBISCO content can survive for long in nature where the $CO_2$ concentration is <0.5%, as the engineered organism has lost most of its ability to scavenge $CO_2$ from the environment. Thus, this risk from inadvertent transgenic release is negated, whether the organism is engineered just for lowered RUBISCO, or engineered with lowered RUBISCO and elevated other enzymes, whether photosynthesis related, or related to other properties.

The present invention relates to the use of algae or cyanobacteria cultivated in ponds or bioreactors that have had their RUBISCO contents transgenically lowered by antisense or RNAi or other transgenic technologies giving rise to similarly lowered RUBISCO contents. These novel organisms are especially adapted to thrive in cultivation with high $CO_2$ levels in the medium, allowing for the over-expression of other, rate limiting enzymes of photosynthesis as well as enzymes encoding for other desirable traits. Thus, these organisms are platforms for further engineering.

In one embodiment the small subunit of RUBISCO is subjected to RNAi suppression and in another it is subjected to antisense. In yet another embodiment both large and small subunits are suppressed by chloroplast transformation of the rbcLS gene cluster under the control of a mutated promoter replacing the endogenous promoter and genes.

In other embodiments DNA encoding other traits is either engineered in tandem with the RUBISCO suppression simultaneously (co-transformation) or subsequent to the engineering of partial RUBISCO suppression. In such embodiments algae or cyanobacteria with reduced RUBISCO levels are used as a platform for further engineering of other desired traits, with greater efficiency of organism activity. These include genes encoding enzymes such as fructose-1,6-bisphosphate aldolase (ALD), chloroplast triosephosphate isomerase (TPI) or acetyl CoA carboxylase (ACCase) that enhance sink capacity to utilize fixed carbon dioxide. Conversely, other transgenic traits may be in the algae or cyanobacteria prior to transformation for partial RUBISCO suppression.

According to one embodiment the alga or cyanobacterium transformed to express reduced RUBISCO content is also transformed to express pharmaceutical or industrial proteins, such as human insulin AAN39451 or AY138590 or thermostable phytase, such as disclosed in U.S. Pat. No. 6,720,174. Other desired proteins to be expressed in transgenic algae or cyanobacteria with reduced RUBISCO content are storage proteins, such as 15 kDZein or BHL8. The transgenic algae expressing reduced RUBISCO content may also be transformed to express altered oil or lipid contents.

A SHORT DESCRIPTION OF THE DRAWINGS

FIG. 1. Map of the plasmid pSI-PDS-rbcS RNAi containing the cassette designed to induce RNAi of *C. reinhardtii* RUBISCO small subunit. An inverted repeat of the first 234 bp of RbcS2 coding region encoding the RUBISCO small subunit is cloned downstream to the pds gene conferring resistance to the herbicide fluorochloridone. The transgene is under the control of the HSP70-RbcS2 promoter and RbcS2 terminator (taken from pDI103, Sizova et al, 2001).

Figure 2:
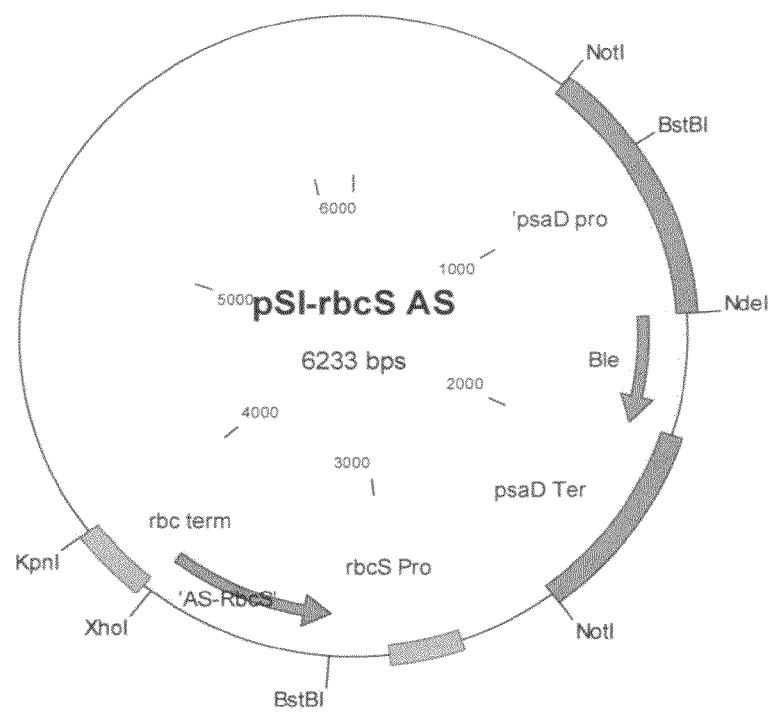

FIG. 2. Map of the plasmid pSI-rbcS-AS containing the cassette designed to induce antisense of *C. reinhardtii* RUBISCO small subunit and the psaD-Ble cassette conferring resistance to the antibiotic Zeocin. The coding region of RbcS2 from *C. reinhardtii* encoding the RUBISCO small subunit is cloned in antisense orientation downstream to the HSP70-rbcS promoter.

DETAILED DESCRIPTION OF THE INVENTION

Algae and cyanobacteria with biotechnological utility are chosen from among the following, non-exclusive list of organisms.
List of Species:
*Pavlova lutheri, Isochrysis* CS-177, *Nannochloropsis oculata* CS-179, *Nannochloropsis* like CS-246, *Nannochloropsis salina* CS-190, *Tetraselmis suecica, Tetraselmis chuii* and *Nannochloris* sp., *Chlamydomonas reinhardtii* as representatives of all algae species. The phylogeny of the algae is summarized in Table 1. *Synechococcus* PCC7002, *Synechococcus* WH-7803, *Thermosynechococcus elongaues* BP-1 are used as representatives of all cyanobactrial species.

Algae and cyanobacteria with partially suppressed RUBISCO are achieved by standard molecular biological procedures, as outlined in numerous texts and papers. First, consensus sequences of the large and small subunits of RUBISCO are used to "fish out" the respective genes by low stringency PCR using a consensus sequences chosen to have the least number of nucleotide variants. Standard software is used to design degenerate primers according to these consensus sequences. After fishing out fragments of the genes, larger segments of the genes are obtained using the RACE (rapid amplification of cDNA ends) technique. The resulting sequences are used to design anti-sense and RNAi constructs that are then inserted into respective cassettes and transformed into the algae and cyanobacteria using techniques readily available to those skilled in the art. Different cassettes are used having different promoters such that a large variety of expression levels are achieved, so that RUBISCO will be reduced by varying amounts. A large number of transformation events were generated for each algal species, and the best transformants chosen as described below.

The growth rates of the transformants are measured under conditions of various levels of high $CO_2$ (1%; 5%; 14%; 100%) and those that appear best are rechecked in mini bioreactors and pilot scale ponds to ascertain which have the best yield, under a variety of environmental conditions and $CO_2$ concentrations.

The best transformants of each organism can then be used as platforms for inserting other genes into the algae or cyanobacteria to optimize the production of valuable compounds. The algae come from a large taxonomical cross section of species (Table 1)

The general approach for green algae is as follows:
1. Cloning of the algae RUBISCO small subunit (rbcS) cDNA in antisense (AS) orientation under the control of a constitutive promoter such as the rbcS promoter and 3'rbcS terminator, downstream to a selectable marker. The selectable marker can be Sh ble, which confers resistance to the antibiotic Zeocine, the pds gene, which confers resistance to fluridone and fluorochloridone.
2. Generation of an RNAi cassette (as described in detail in Schroda, 2006) of the algae rbcS gene comprising a 300 bp cDNA/cDNA inverted repeat under the control of a constitutive promoter downstream to a selectable marker described above.

The general approach for red lineage marine algae species (Sub-kingdom Chromobiota, Table 1), is to replace the chloroplast RUBISCO small or large subunit with a DNA construct containing the same RUBISCO subunit gene controlled by a mutated promoter, use antisense or with a chloroplast expression vector, and directly transform the chloroplasts, as has been done with Chlamydomonas (Franklin and Mayfield, 2004)

The general approach for cyanobacteria is as follows:
Cloning of the RUBISCO small subunit (rbcS) or large subunit (rbcL) gene from a cyanobacteria species under the control of mutated promoter and replacing the respective endogenous gene with the cloned cassette using homologous recombination, as described in Clerico et al. (2007).

The methodology used in the various steps of enabling the invention is described here below:

Nucleic Acid Extraction Genomic DNA is isolated using either the Stratagene (La Jolla, Calif., USA) DNA purification kit or a combination of the QIAGEN (Valencia, Calif., USA) DNeasy plant mini kit and phenol chloroform extraction method (Davies et al. 1992). Total RNA is isolated using either the QIAGENS Plant RNeasy Kit or the Trizol Reagent (Invitrogen, Carlsbad, Calif., USA).

RACE analysis The full length RbcS small and large subunits from algae or cyanobacteria with unknown genomic sequences are determined by 3' and 5' RACE and nested PCR using the First Choice RLM-RACE Kit (Ambion, Austin, Tex., USA), as described by Liu and Gorovsky (1993).

Transformation of Plasmid DNA

Transformation of Chlamydomonas Algae cells in 0.4 mL of growth medium containing 5% PEG (polyethylene glycol MW6000) were transformed with the plasmid from examples 1 and 2 by the glass bead vortex method (Kindle, 1990). The transformation mixture was then transferred to 50 mL of non-selective growth medium for recovery and incubated for at least 18 h at 25° C. in the light. Cells were collected by centrifugation and plated at a density of $10^8$ cells per Petri dish. Transformants were grown on fresh TAP or SGII agar plates containing a selection agent for 7-10 days in 25° C.

Transformation of Marine Algae

I. Electroporation

Fresh algal cultures are grown to mid exponential phase in artificial sea water (ASW)+f/2 media. Cells are then harvested and washed twice with fresh media. After resuspending the cells in 1/50 of the original volume, protoplasts are prepared by adding an equal volume of 4% hemicellulase (Sigma) and 2% Driselase (Sigma) in ASW and are incubated at 37° C. for 4 hours. Protoplast formation is tested by Calcofluor white (Fluka) staining. Protoplasts are washed twice with ASW containing 0.6M D-mannitol (Sigma) and 0.6M D-sorbitol (Sigma) and resuspended in the same media, after which DNA is added (10 µg linear DNA for each 100 µl protoplasts). Protoplasts are transferred to cold electroporation cuvettes and incubated on ice for 7 minutes, then pulsed in a BTX ECM830 (Harvard Apparatus, Holliston, Mass., USA) electroporation apparatus. A variety of pulses is usually applied, ranging from 1000 to 1500 volts, 10-20 ms each pulse. Each cuvette is pulsed 5-10 times. Immediately after pulsing the cuvettes are placed on ice for 5 minutes and then the protoplasts are added to 250 µl of fresh growth media (without selection). After incubating the protoplasts for 24 hours in low light, 25° C. the cells are plated onto selective solid media and incubated under normal growth conditions until single colonies appear.

II. Microporation

A fresh algal culture is grown to mid exponential phase in ASW+f/2 media. A 10 mL sample of the culture is harvested, washed twice with Dulbecco's phosphate buffered saline (DPBS, Gibco) and resuspended in 250 µl of buffer R (supplied by Digital Bio, Seoul, Korea, the producer of the microporation apparatus and kit). After adding 8 µg linear DNA to every 100 µl cells, the cells are pulsed. A variety of pulses is usually needed, depending on the type of cells, ranging from 700 to 1700 volts, 10-40 ms pulse length; each sample is pulsed 1-5 times. Immediately after pulsing the cells are transferred to 200 µl fresh growth media (without selection). After incubating for 24 hours in low light, 25° C., the cells are plated onto selective solid media and incubated under normal growth conditions until single colonies appear.

III. Particle Bombardment

A fresh algal culture is grown to mid exponential phase in ASW+f/2 media. 24 hours prior to bombardment cells are harvested, washed twice with fresh ASW+f/2 and re-suspended in 1/10 of the original cell volume in ASW+f/2. 0.5 mL of each cell suspension is spotted onto the center of a 55 mm Petri dish containing 1.5% agar solidified ASW+f/2 media. Plates are left to dry under normal growth conditions. Bombardment is carried out using a BioRad PDS1000/He system according to the manufacturer's (BioRad) instructions, using M10 tungsten powder for cells larger than 2 microns in diameter, and tungsten powder comprised of particles smaller than 0.6 microns (FW06, Canada Fujian Jinxin Powder Metallurgy Co., Markham, ON, Canada) for smaller cells. The tungsten is coated with linear DNA. 1100 or 1350 psi rupture discs are used. All disposables are supplied by BioRad. After bombardment the plates are incubated under normal growth conditions for 24 hours followed by transferring the cells onto selective solid media and incubated under normal growth conditions until single colonies appear. For chloroplast transformation, this method is carried out in the same way, but the resulting transformants are screened for the presence of the transgene in the chloroplast.

Transformation of Cyanobacteria

For transformation to *Synechococcus* PCC7002, cells are cultured in 100 mL of BG-11+Turks Island Salts liquid medium (http://www.crbip.pasteur.fr/fiches/fichemediumjsp?id=548) at 28° C. under white fluorescent light and cultured to mid exponential growth phase. To 1.0 mL of cell suspension containing $2 \times 10^8$ cells, 0.5-1.0 µg of donor DNA (in 10 mM Tris/1 mM EDTA, pH 8.0) is added, and the mixture is incubated in the dark at 26° C. overnight. After incubation for a further 6 h in the light, the transformants are selected on BG-11+Turks Island Salts 1.5% agar plates containing a selection agent until single colonies appear.

There is no prior art known to us of previously transforming the following species: *Pavlova lutheri*, *Isochrysis* CS-177, *Nannochloropsis oculata* CS-179, *Nannochloropsis* like CS-246, *Nannochloropsis salina* CS-190, *Tetraselmis suecica*, *Tetraselmis chuii* and *Nannochloris* sp. nor has microporation been used previously for transforming algae cyanobacteria or higher plants.

RNA extraction, cDNA synthesis and quantitative RT-PCR analysis Total RNA is isolated using either the QIAGENS Plant RNeasy Kit or the Trizol Reagent (Invitrogen, Carlsbad, Calif., USA). cDNA is synthesized using 3 µg total RNA as a template using SuperscriptII kit (Invitrogen, Carlsbad, Calif., USA) according to the manufacturer's instructions. Real-time quantitative PCR reactions are preformed in an optical 96-well plate using the ABI PRISM 7300 Sequence Detection System (Applied Biosystems, Scoresby, Victoria, Australia) and SYBR Green I for monitoring dsDNA synthesis. For all PCR reactions the following standard thermal profile is used: 50° C. for 2 min; 95° C. for 15 min; 40 cycles of 95° C. for 15 sec and 60° C. for 1 min. In order to compare data from different cDNA samples, $C_T$ (threshold cycle) values for all genes are normalized to the $C_T$ values of Ubiquitin, or 16S rDNA for algae and cyanobacteria, respectively, which are used as internal references in all experiments. All primers are designed using the Primer Express 2.0 software (Applied Biosystems, Foster City, Calif., USA). The sequences of sense and antisense designed primers correspond to two consecutive exons of the studied genes, excluding any genomic DNA amplification. The real-time PCR data is analyzed using the comparative CT-method with appropriate validation experiments performed beforehand (Applied Biosystems, User Bulletin #2, http://home.appliedbiosystems.com/). All experiments are repeated at least three times with cDNA templates prepared from three independent colonies of algae or cyanobacteria and every reaction is set up in triplicates.

Protein extraction 1 to 10 mL cells at $5 \times 10^6$ cell/mL are harvested and resuspended in 500 µl extraction buffer (50 mM Tris pH=7.0; 1 mM EDTA; 100 mM NaCl; 0.5% NP-40; and protease inhibitor (Sigma cat# P9599). Then 100 µl of glass beads (425-600 µm, Sigma) are added and cells are broken in a bead beater (MP FastPrep-24, MP Biomedicals, Solon, Ohio, USA) for 20 sec. The tube content is centrifuged for 15 min, 13000×g, at 4° C. The supernatant is removed to new vial.

Protein separation by PAGE and western analysis Extracted proteins are separated on a 4-20% gradient SDS-PAGE (Gene Bio-Application Ltd., Kfar Hanagid, Israel, at 160V for 1 hr. They were then either stained by Coomassie (Sigma) or blotted onto PVDF (Millipore, Billerica, Mass., USA) membranes for 1 h at 100 volts in the transfer buffer (25 mM Tris, 192 mM glycine and 20% methanol). The proteins are detected with the RbcL RUBISCO large subunit, form I and form II antibody (Agrisera, Vännäs, Sweden) diluted to a ratio of 1:10000 in antibody incubation buffer (5% skim milk, Difco). An alkaline phosphatase conjugated anti-rabbit antibody (Millipore, Billerica, Mass., USA), at 1:10000 dilution in the same buffer was used as a secondary antibody. Detection was carried out using the standard alkaline phosphatase detection procedure (Blake et al., 1984).

Physiological Assessment To assess physiological properties of genetically modified algae compared with their relevant wild type strains and other algal candidates we perform a set of procedures that enable us to evaluate each strain. Initially, each genetically modified strain is checked for the modified trait, (reduced RUBISCO content). A screening process is established where colonies of transgenic algae or cyanobacteria are allowed to grow on solid media supplemented with selection reagent (an antibiotic or herbicide) to check if the desired trait has been established. Next, the fastest growing colonies are picked and transferred to liquid medium for further physiological evaluation.

This includes:
1. Growth rate
2. Photosynthetic activity at ambient and high carbon dioxide concentrations
3. Respiration activity
4. Tolerance to a-biotic parameters
5. Lipid content
6. Protein content An overall report is generated for each strain that is used to estimate the feasibility of using the strain.

Growth Rate Growth rates are measured using one or more of the following techniques:
Direct cell count
Optical density at a relevant wavelength (e.g. 730 nm)
Pigment/Chlorophyll concentration (where this method is applicable)
Percentage of packed volume Photosynthetic Activity One of the important parameters indicating the welfare of a photoautotrophic culture is its photosynthetic capability. To measure this, one or more of several methodologies are applied:
Oxygen evolution—using Clark Type electrodes.
Variable fluorescence—using PAM (Pulse Amplitude Modulated fluorometry)

Oxygen consumption in darkness is also evaluated in order to estimate net photosynthetic potential of the algal culture. As part of the photosynthetic evaluation several abiotic parameters that potentially influence the physiological state of a culture are followed.
Light intensity tolerance (at a given cell density) is evaluated. P/I (photosynthesis vs. irradiance) curves are used to determine optimal light intensity per cell.
Performance at different $CO_2$ levels (e.g. ambient; 1%; 5%; 14%; 100%). This is coupled with pH tolerance.

Temperature tolerance. Each culture is tested at optimal temp. In addition, temperatures are raised temperatures to the highest points possible without inhibiting other culture activities.

Growth conditions Cells of eukaryotic marine cultures and transformants thereof are grown on artificial seawater medium (Goyet, 1989) supplemented with f/2 (Guillard, 1962). Marine cultures are grown at 18-20° C. with a 16/8 h light/dark period. Fresh water cultures (e.g. the diploid wild-type *Chlamydomonas reinhardtii*) and transformants thereof are grown photoautotrophically on liquid medium, using mineral medium as previously described (Harris, 1989), with the addition of 5 mM $NaHCO_3^-$, with continuous shaking and illumination at 22° C. Marine cyanobactertial cultures and transformants thereof are grown in BG11 medium BG11 (Stanier et al., 1971) supplemented with Turks Island Salts and with 20 mM HEPES-NaOH buffer pH 7.8 (http://www.crbip.pasteur.fr/fiches/fichemedium.jsp?id=548). Cyanobacterial cultures are grown at 25° C. where relevant under continuous white light, with constant $CO_2$-air bubbling.

Growth Rate Estimation Cells are harvested in the logarithmic growth phase and re-suspended in fresh growth media. Cultures are brought to a cell density corresponding to ~3 µg/mL chlorophyll a. Light intensity is optimized for each culture and temperature is maintained at growth temperature ±1° C. Where required, cells are concentrated by centrifugation (3000 g, 5 min) and re-suspended in fresh media. A time-series sampling procedure is followed where a sub-sample of each culture is collected and the number of cells per mL is estimated. As well as direct counting, optical density at different wavelengths, percentage of packed volume and chlorophyll concentrations are also measured.

Photosynthetic Activity: Oxygen evolution Measurements of $O_2$ concentrations are performed using a Clark type $O_2$ electrode (Pasco Scientific, Roseville, Calif., USA). Twenty mL of cell suspension containing 15 µg chlorophyll/mL are placed in the $O_2$ electrode chamber, at relevant temperature. Cells are exposed to various light intensities and regimes (e.g. flashing light). Incubations in darkness are performed in these air-tight vessels to follow oxygen consumption in the dark.

Fluorescence measurements Electron transfer activity of photosystem II is measured by pulse modulated fluorescence (PAM) kinetics using PAM-101 (Walz, Effertlich, Germany). Light intensity (measured at the surface of the chamber) of the modulated measuring beam (at 1.6 kHz frequency) is 0.1 µmol photons $m^{-2}$ $s^{-1}$. White actinic light is delivered at 50-1500 µmol photons $m^{-2}$ $s^{-1}$ as required in different experiments and is used to assess steady state fluorescence ($F_s$). Maximum fluorescence ($F_m$) is measured with saturating white light pulses of 4000 µmol photons $m^{-2}$ $s^{-1}$ for 1 s.

Additional Experiments

Light intensity tolerance (at a given cell density) is evaluated. P/I (photosynthesis vs. irradiance) curves are used to determine optimal light intensity per cell. Four mL of cell suspension containing 15 µg chlorophyll/mL are placed in the $O_2$ electrode chamber, at relevant temperatures and various light intensities. Oxygen evolution rates are measured at each light intensity.

Performance at different $CO_2$ levels (e.g. ambient; 1%; 5%; 14%; 100%). Growth rate estimations and photosynthetic activity (methodology described above) are evaluated when cultures are maintained at different $CO_2$ levels.

Temperature tolerance. Each culture is tested at optimal temp. In addition, we attempt to raise temperatures to the highest point possible without inhibiting other culture activities.

The invention is now described by means of various non limiting examples using the above methods:

EXAMPLE 1

Generation of *C. reinhardtii* Expressing RNAi of RbcS2B Gene Under the Control of the HSP70-rbcS2 Promoter For generation of RNAi of rbcS2 (ACCESSION NO: X04472), a 774 bp fragment (SEQ ID NO:1) corresponding to forward and reverse orientation of nucleotides 1 to 234 of rbcS2 gene separated by 246 bp spacer region comprised from the $3^{rd}$ intron of the rbcS2 gene (REGION: 1947.2184), was custom synthesized by DNA2.0 Inc, (Menlo Park, Calif., USA). The 774 bp region (SEQ OD NO:1) was then cloned into BamHI restriction site in plasmid pSI-PDS downstream to the pds gene, generating the plasmid pSI-PDS rbcS RNAi (FIG. 1).

The plasmid was transformed to *C. reinhardtii* CW15 strain (CC-400) and transfromants were selected on SGII medium supplemented with 3×10⁷ M fluorochloridone (FCD). FCD resistant colonies were transferred to liquid media for DNA and protein extraction. *Tetraselmis suecica*, *Tetraselmis chuii* and *Nannochloris* sp are transformed with the above cassette using to the transformation methods described above. Total proteins are separated on 4-20% gradient SDS-PAGE (Geba, Israel) and stained with Coomassie blue or transferred to PVDF membranes (Millipore, Billerica, Mass., USA) for western blot analysis using the anti RbcL RUBISCO large subunit, form I and form II antibody (Agrisera, Vannas, Sweden).

Colonies with reduced RUBISCO levels are further analyzed as described in examples 5 to 7.

EXAMPLE 2

Generation of *C. reinhardtii* Expressing the rbcS2 Gene in Antisense Orientation Under the Control of the HSP70-rbcS2 Promoter For the generation of plasmids containing the *C. reinhardtii* rbcS2 gene in antisense orientation under the control of the HSP70-rbcS2 promoter (FIG. 2), the 579 bp fragment of the *C. reinhardtii* rbcS2 gene was PCR amplified with primers BstBI-rbcS2B: GCTTCGAATCAACGAGCGC-CTCCATTTAC (SEQ ID NO:2), and XhoI-rbcS2 AS GCCTCGAGATGGCCGCCGTCATTGCCAA (SEQ ID NO:3) containing the BstBI and XhoI sites at their 5' and 3' regions, respectively, and was cloned into pGEM-T vector (Promega, Madison, Wis., USA). The BstBI-XhoI fragment was then introduced into the BstBI/XhoI sites of plasmid pSI-PDS rbcS RNAi, replacing the pds-rbcS RNAi cassette (Example 1). A psaD-Ble fragment (comprising the Ble selectable marker (SEQ ID NO: 4) under the control of the psaD promoter (SEQ ID NO:5), excised from pGenD-Ble) was further ligated into the plasmid using NotI restriction site. The resulting pSI-rbcS-AS plasmid was then transformed to *C. reinhardtii* CW15 (CC-400) and transformants were selected on TAP medium supplemented with 5 µg/mL Zeocin. Approximately 100 Zeocin resistant colonies were transferred to liquid media for protein extraction and rbcS level analysis.

*Tetraselmis suecica*, *Tetraselmis chuii* and *Nannochloris* sp are transformed with the above cassette using to the transformation methods described above. Colonies with reduced RUBISCO levels are further analyzed as described in examples 5 to 7.

EXAMPLE 3

Generation of Cyanobacterial Transformants with Reduced Rubisco Expression Levels In order to reduce expression level of rbcL in the cyanobacterium *Synechococcus* PCC7002, the native rbcL promoter is replaced with a mutated one. The rbcL region (SEQ ID NO: 6) is synthesized with random mutations in the promoter region (nucleotides 1165-1638 in SEQ ID NO: 6) and a spectinomycin resistance cassette upstream of the promoter. Resulting fragments are then cloned into pGEM-T (Promega, Madison, Wis., USA) to create a library of plasmids containing a myriad of mutated promoters. The resulting library is transformed into *Synechococcus* PCC7002, and following homologous recombination (that occurs naturally in cyanobacteria) clones are screened for transformants with reduced RUBISCO content.

EXAMPLE 4

Chloroplast Transformation of Red Lineage Algae

To reduce rbcS expression level of red lineage marine algae, the sequence of the algae chloroplast DNA is obtained using 454 sequencing (CD Genomics, Shirley, N.Y., USA). Then, a DNA fragment containing the rbcS gene and its flanking regions is obtained by PCR on DNA isolated from the marine algae. The rbcS coding sequence is then cloned under a mutated rbcL promoter and rbcL terminator together with a spectinomycin resistance gene cassette comprising rbcL promoter, bacterial AAD gene (SEQ ID NO:7) and rbcL terminator as described in Takahashi, (1991). This construct is then transformed to the algae chloroplast DNA using particle bombardment as described in the methods part, and according to Spectinomycin resistant colonies are then selected and analyzed using PCR on genomic DNA to confirm the homologous recombination. Positive colonies are then selected for further analysis as described in Examples 5-7.

EXAMPLE 5

Demonstration that Transformed Algae and Cyanobacteria have Optimal Photosynthesis at Elevated $CO_2$ Cultures of reduced RUBISCO-content transformants of algae and cyanobacteria are compared to those of their respective wild type. While the latter reveal maximal photosynthesis rates at concentrations of 0.03-1% $CO_2$, transformed algal and cyanobacterial cells exhibit maximal photosynthesis rates at $CO_2$ concentrations above 4%. The increased $CO_2$ concentrations compensated for reduced RUBISCO contents.

EXAMPLE 6

Demonstration that Transformed Algal and Cyanobacterial Strains Cannot Compete with Wild Type Cultures at Ambient $CO_2$ Concentrations The algal and cyanobacterial transformants described above function best under bioreactor and/or pond conditions at high $CO_2$ concentrations. An additional benefit arising from this condition is that these strains cannot cope with natural occurring conditions such as ambient $CO_2$ concentration. Being currently at 0.03% in the atmosphere, $CO_2$ becomes a major limiting factor for the transformants cultured with ambient carbon dioxide levels. In order to demonstrate such growth limitation reduced-RUBISCO-content transformants are co-cultured with wild-type cells at ambient $CO_2$ concentrations. A time-sequence sampling protocol is followed and cells are collected from the growth vessels. Cells are then transferred to plates for colony isolation, then replicas are made of each colony. One plate contains normal growth media while its duplicate contained a selection factor (e.g. antibiotics/herbicides). This enables the differentiation between wild-type cells and transformants, allowing following wild-type cells outcompeting reduced RUBISCO content transformants co-cultivated under ambient carbon dioxide.

EXAMPLE 7

Demonstration that Transformed Algal and Cyanobacterial Strains have Increased Levels of Photosynthesis when Sink-Enhancing Genes are Transformed into These Strains Reduced-RUBISCO-content transgenic algae and cyanobacteria are further transformed with sink-enhancing genes. As was previously demonstrated by Miyagawa et al., (2001), overexpression of cyanobacteria fructose-1,6-/sedoheptulose-1,7-bisphosphatase (FBP/SBPase) (SEQ ID NO:8) in tobacco enhances photosynthesis and growth, is used. The reduced-RUBISCO-content×FBP/SBPase transformants are compared with the reduced-RUBISCO-content transformants alone under conditions of 14% $CO_2$. Oxygen evolution is followed as an indication for photoautotrophic assimilation, and higher oxygen production rates are observed with the reduced-RUBISCO-content×FBP/SBPase transformants. This implies higher Ci assimilation rates, and therefore suggests enhanced energy harvesting even at when RUBISCO levels are reduced.

Growth Rate Estimation

Cultures of Reduced-RUBISCO-Content (RRC) transformants of green algae (*Tetraselmis suecica, Tetraselmis chuii, Nannochloris* sp. and *Chlamydomonas reinhardtii*) are compared to those of their respective wild type. Wild type cells reveal a saturation-curve-like pattern where growth rates increase with increasing $CO_2$ concentrations. At ambient $CO_2$ concentrations, reduced-RUBISCO-content cells exhibit reduced growth rates. Their doubling times are reduced (at ambient $CO_2$) but increased with increasing $CO_2$ concentrations.

Photosynthetic Activity:

Oxygen Evolution and PAM Fluorescence

Again, cultures of Reduced-RUBISCO-Content transformants of green algae (*Tetraselmis suecica, Tetraselmis chuii, Nannochloris* sp and *Chlamydomonas reinhardtii*) are compared to those of their respective wild type. Wild-type cells reveal a typical P/I saturation curve. In contrast, reduced-RUBISCO-content cells exhibit a slight decrease in optimal light intensity, i.e. saturation and inhibition occurs at lower light intensities. When $CO_2$ levels are raised to 14% or more, P/I curves of reduced-RUBISCO-content cells return to normal parameters. The increase of $CO_2$ concentrations compensates for the reduced RUBISCO content.

Lipid and Protein Contents

Finally, we test reduced-RUBISCO-content transformants for lipid and protein content, and compare them to those of wild type cells. Lipid and protein content are lower in the transformants than in wild type cells at ambient $CO_2$ concentrations. However, when $CO_2$ levels are increased to 14% or more, lipid and protein contents exceed those of wild type cells.

REFERENCES

Blake M S, Johnston K H, Russell-Jones G J and Gotschlich E C. (1984) A rapid, sensitive method for detection of alkaline phosphatase-conjugated anti-antibody on Western blots. Anal Biochem 136:175-9.

Clerico E M, Ditty J L, Golden S S (2007) Specialized techniques for site-directed mutagenesis in cyanobacteria. Methods Mol Biol 362: 155-171.

Deng M D, Coleman J R (1999) Ethanol synthesis by genetic engineering in cyanobacteria. Appl Environ Microbiol 65:523-528

Falkowski, P G and Raven J A (1997) Aquatic Photosynthesis. Blackwell Science. Malden, Mass. 373, 705-509.

Franklin S E and Mayfield S P. (2004) Prospects for molecular farming in the green alga Chlamydomonas reinhardtii. Curr Opin Plant Biol, 7:159-165.

Grzebyk, D., Schofield O., Falkowski P., and J. Bernhard (2003) The Mesozoic radiation of eukaryotic algae: the portable plastid hypothesis. J Phycol 39:259-267

Harris, E. (1989). The Chlamydomonas Sourcebook: a Comprehensive Guide to Biology and Laboratory Use, Academic Press.

Helman, Y., Tchernov, D., Reinhold, L., Shibata, M., Ogawa, T., Schwarz, R., Ohad, I. and Kaplan, A. (2003) Genes encoding A-type flavoproteins are essential for photoreduction of $O_2$ in cyanobacteria. Curr Biol 13: 230-235

Huntley M. E. and Redalje, D. G. (2007). $CO_2$ mitigation and renewable oil from photosynthetic microbes: A new appraisal, Mitig. Adapt. Strateg. Glob. Change 12, 573-608.

Kang R J, Shi D J, Cong W, Ma W M, Cai Z L, Ouyang F. (2005) Effects of co-expression of two higher plants genes ALD and TPI in Anabaena sp. PCC7120 on photosynthetic $CO_2$ fixation. Enzym Microb Tech 36: 600-604.

Kindle K L (1990) High-frequency nuclear transformation of Chlamydomonas reinhardtii. PNAS 87:1228.

Liu X, and Gorovsky M A (1993) Mapping the 5' and 3' ends of Tetrahymena thermophila mRNAs using RNA ligase mediated amplification of cDNA ends (RLM-RACE). Nucl Acids Res 21: 4954-4960.

Lumbreras V, Stevens D. and, Purton S (1998) Efficient foreign gene expression in Chlamydomonas reinhardtii mediated by an endogenous intron. Plant J 14: 441-447.

Ma, V M, Wei, L, Wang, Q, Shi, D and Chen, H. (2007) Increased activity of the non-regulated enzymes fructose-1,6-bisphosphate aldolase and triosephosphate isomerase in Anabaena sp strain PCC 7120 increases photosynthetic yield, J Appl Phycol 19:207-213.

Miyagawa, Y. Tamoi, M. and Shigeoka. S. (2001) Overexpression of a cyanobacterial fructose-1,6-/sedoheptulose-1,7 bisphosphatase in tobacco enhances photosynthesis and growth. Nature 19: 965-969.

Murakami M. and Ikenouchi M. (1997) The biological $CO_2$ fixation and utilization project by RITE (2)—Screening and breeding of microalgae with high capability in fixing $CO_2$. Energy Conyers Mgmt. 38: S493-S497.

Negoro, M, Hamansaki, A, Ikuta, Y Makita, T, Hirayama, K. and Suzuki, S. (1993) Carbon dioxide fixation by microalgae photosynthesis using actual flue gas discharged from a boiler, 39: 643-653.

Prentki P and Krisch H M (1984) In vitro insertional mutagenesis with a selectable DNA fragment. Gene 29: 303-313

Schroda M. (2006) RNA silencing in Chlamydomonas: mechanisms and tools. Curr Genet. 49: 69-84

Sizova, I, Fuhrmann, M, and Hegemann, P. (2001) A Streptomyces rimosus aphVIII gene coding for a new type phosphotransferase provides stable antibiotic resistance to Chlamydomonas reinhardtii. Gene 277: 221-229.

Stanier, R Y, Kunisawa, R, Mandel, M and Cohen-Bazire, G. (1971) Purification and properties of unicellular bluegreen algae (order Chroococcales). Bacteriol. Rev. 35: 171-205.

Y. Takahashi, M. Goldschmidt-Clermont, S.-Y. Soen, L. G. Franzenl and J.-D. Rochaix. (1991) Directed chloroplast transformation in Chiamydomonas reinhardtii: insertional inactivation of the psaC gene encoding the iron sulfur protein destabilizes photosystem I. EMBO J. 10: 2033-2040.

Wyman, M, Gregolry, R P F, and Carr, N G. (1985) Novel role for phycoerythrin in a marine cyanobacterium, Synechochoccus strain DC2. Science 230: 818-820.

What is claimed is:

1. A method for transforming algal or cyanobacterial cells, comprising mixing a polynucleotide for transforming the cells with the polynucleotide; performing microporation by applying a plurality of electrical pulses to the cells with a microporation apparatus; and incubating said polynucleotide with the cells after said applying said electrical pulses.

2. The method of claim 1, wherein said performing microporation by said applying said plurality of electrical pulses comprises applying pulses having a voltage in a range of from 700 to 1700 volts.

3. The method of claim 2, wherein said applying said pulses comprises applying pulses having a pulse length in a range of from 10 to 40 ms.

4. The method of claim 3, wherein said applying said plurality of electrical pulses comprises applying said electrical pulses 1-5 times.

5. The method of claim 4, wherein said mixing comprises suspending the cells in a solution; and mixing said polynucleotide with said solution.

6. The method of claim 5, wherein said mixing comprises mixing a linear DNA polynucleotide with the cells.

7. The method of claim 5, wherein said suspending the cells in said solution comprises suspending the cells in a solution that does not remove the cell wall, such that said performing said microporation comprises applying said plurality of electrical pulses to the cells with cell walls.

* * * * *

SEQUENCE LISTING

```
<160> NUMBER OF SEQ ID NOS: 8

<210> SEQ ID NO 1
<211> LENGTH: 774
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(774)
<223> OTHER INFORMATION: RNAi cassette for Chlamydomonas reinhardtii
      RbcS2 gene, encodes for ribulose-1,5-bisphosphate
      carboxylase/oxygenase (RUBISCO) small subunit 2:

<400> SEQUENCE: 1
ggatcctcta gagtcactca acatcttaaa atggccgccg tcattgccaa gtcctccgtc      60
tccgcggccg tggcccgccc ggcccgctcc agcgtgcgcc ccatggccgc gctgaagccc     120
```

```
gccgtcaagg ccgcccccgt ggctgccccg gctcaggcca accagatgat ggtctggacc    180
ccggtcaaca acaagatgtt cgagaccttc tcctacctgc ccccctgag cgacgagcag     240 atcgccgccc aggtcgacta cattgtaagt ctggcgagag cccgacgggt ccactgtggc    300
actgggttag cttttggcac acgggtccac tgtggcactg gttagcttgg caccgggaca    360
gcgcctatct caccgcgggg aactgacgca tacccctgct cgtgcttcag cacggaaaag    420 caagggccc aattccatct ttggtggttc tgtgcgctgg tgactgaacc tcttctccct     480
cccatttccc gtgcgcccgc agctgtacta aatgtagtcg acctgggcgg cgatctgctc    540
gtcgctcagg gggggcaggt aggagaaggt ctcgaacatc ttgttgttga ccggggtcca    600
gaccatcatc tggttggcct gagccggggc agccacgggg gcggccttga cggcgggctt    660
cagcgcggcc atgggcgca cgctggagcg ggccgggcgg gccacggccg cggagacgga    720
ggacttggca atgacggcgg ccattttaag atgttgagtg actctagagg atcc          774

<210> SEQ ID NO 2
<211> LENGTH: 29
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(29)
<223> OTHER INFORMATION: primer BstBI-rbcS2B

<400> SEQUENCE: 2
gcttcgaatc aacgagcgcc tccatttac                                       29

<210> SEQ ID NO 3
<211> LENGTH: 28
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(28)
<223> OTHER INFORMATION: primer Xho1-rbsS2 AS

<400> SEQUENCE: 3
gcctcgagat ggccgccgtc attgccaa                                        28

<210> SEQ ID NO 4
<211> LENGTH: 375
<212> TYPE: DNA
<213> ORGANISM: Pichia pastoris
<220> FEATURE:
<221> NAME/KEY: misc_feature
<222> LOCATION: (1)..(375)
<223> OTHER INFORMATION: bleomycin binding protein(Ble) gene sequence

<400> SEQUENCE: 4
atggccaagt tgaccagtgc cgttccggtg ctcaccgcgc gcgacgtcgc cggagcggtc     60
gagttctgga ccgaccggct cgggttctcc cgggacttcg tggaggacga cttcgccggt    120
gtggtccggg acgacgtgac cctgttcatc agcgcggtcc aggaccaggt ggtgccggac    180
aacaccctgg cctgggtgtg ggtgcgcggc ctggacgagc tgtacgccga gtggtcggag    240
gtcgtgtcca cgaacttccg ggacgcctcc gggccggcca tgaccgagat cggcgagcag    300
ccgtgggggc gggagttcgc cctgcgcgac cggccggaca ctgcgtgca cttcgtggcc    360 gaggagcagg actga                                                     375
```

<210> SEQ ID NO 5
<211> LENGTH: 822
<212> TYPE: DNA
<213> ORGANISM: Chalmydomonas sp.
<220> FEATURE:
<221> NAME/KEY: promoter
<222> LOCATION: (1)..(822)
<223> OTHER INFORMATION: Chlamydomonas psaD promoter

<400> SEQUENCE: 5

| | | | | | | |
|---|---|---|---|---|---|---|
| gcggccgcca | cacacctgcc | cgtctgcctg | acaggaagtg | aacgcatgtc | gagggaggcc | 60 |
| tcaccaatcg | tcacacgagc | cctcgtcaga | aacacgtctc | cgccacgctc | tccctctcac | 120 |
| ggccgacccc | gcagccctttt | tgcccttttcc | taggccaccg | acaggaccca | ggcgctctca | 180 |
| gcatgcctca | acaacccgta | ctcgtgccag | cggtgcccctt | gtgctggtga | tcgcttggaa | 240 |
| gcgcatgcga | agacgaaggg | gcggagcagg | cggcctggct | gttcgaaggg | ctcgccgcca | 300 |
| gttcgggtgc | ctttctccac | gcgcgcctcc | acacctaccg | atgcgtgaag | gcaggcaaat | 360 |
| gctcatgttt | gcccgaactc | ggagtcctta | aaaagccgct | tcttgtcgtc | gttccgagac | 420 |
| atgttagcag | atcgcagtgc | cacctttcct | gacgcgctcg | gccccatatt | cggacgcaat | 480 |
| tgtcatttgt | agcacaattg | gagcaaatct | ggcgaggcag | taggcttttta | agttgcaagg | 540 |
| cgagagagca | aagtgggacg | cggcgtgatt | attggtatttt | acgcgacggc | ccggcgcgtt | 600 |
| agcggccctt | cccccaggcc | agggacgatt | atgtatcaat | attgttgcgt | tcgggcactc | 660 |
| gtgcgagggc | tcctgcgggc | tggggagggg | gatctgggaa | ttggaggtac | gaccgagatg | 720 |
| gcttgctcgg | ggggaggttt | cctcgccgag | caagccaggg | ttaggtgttg | cgctcttgac | 780 |
| tcgttgtgca | ttctaggacc | ccactgctac | tcacaacaag | cc | | 822 |

<210> SEQ ID NO 6
<211> LENGTH: 3001
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(3001)
<223> OTHER INFORMATION: Synechococcus PCC7002 rbcL region

<400> SEQUENCE: 6

| | | | | | | |
|---|---|---|---|---|---|---|
| tttcaacgag | ggcaggcatg | tgccatacgt | ggataccacc | ggaagccaca | ggcatggtgc | 60 |
| cggggagaga | agcgtagtct | tgggtgaaga | atacaccgcg | agaacgatct | tcttcaacgt | 120 |
| agtcttcacg | catcaggtct | acgaaaccga | gggtggcggc | gcgatcgcct | tcgagcttac | 180 |
| caacaaccgt | accggagtgg | aggtggtcac | caccagagag | gcggagacac | ttagcgagaa | 240 |
| cgcggaagtg | aataccgtgg | ttcttctgac | ggtcgattac | cgcgtgcatt | gcccggtgga | 300 |
| tgtggagcag | aacgccgtta | tcacgacacc | acttcgcaag | ggtagtattc | gcagtgaaac | 360 |
| caccagttaa | gaagtcgtgc | atgatgatgg | gagtgccgat | ttccttagcg | aattcagccc | 420 |
| gcttgagcat | ttcttcgcaa | gtgccagcgg | tgacgttaag | gtagtgaccc | ttaacttcgt | 480 |
| tggtttcagc | ttgggatttt | tcgatagctt | cttgaacgaa | caggaagcga | tcgcgccaac | 540 |
| gcatgaaagg | ctgagagttg | atgttttcgt | catctttggt | gaagtcaaga | ccaccacgga | 600 |
| gacattcata | aaccgcacga | ccgtagttct | tcgcagacag | accgagcttc | ggcttaatcg | 660 |
| tacaaccgag | gagaggacga | ccatacttgt | tgaggaggtc | acgctctaca | gtgatcccgt | 720 |
| ggggaggccc | ttggtaagtt | ttgattaacg | caacggggaa | gcggatatct | tcgaggcgca | 780 |

```
gggcacgcag cgctttaaaa ccgaatacgt taccaaccaa ggaagtcaaa acgttggtta    840
cagaaccttc ttcaaacaga tcgaggggat aagcaacgaa acagaaatat tggttgtctt    900
caccgggaac gggttcaaca ttgtagcaac gacccttgta gcggtcgagg tcagttaaac    960
catcggtcca tacagtggtc caagtaccgg tagaagattc agccgcaaca gccgcagcac   1020
attcttcggg ggggactcca ggttggggag tcatccggaa acaagcgagt aagtcggtat   1080
ctttcggggt gtaatcgggg gtgtagtaag tcaggcggta gtcctgtaca ccggcattaa   1140
acccagcaga tttggtctga accatgcggt tttcctccag caaaaatgct tatctttaac   1200
agacaaatac cagtaacggt attgttggtc gaaaacttca aaaatcttac gttggcaaaa   1260
ctgcttttta aaattctgaa gattcaagtc ttatgacttt ctttaatctg tgggatatgt   1320
taccacagcc tcgacttatt tttatctttt agcaacaaaa aaagattgct tttgtttttt   1380
gggctgatta gcatttctaa tgctgtttga tgggcctatt ttaccccttac aaaaatacct   1440
aaaaaagcca taaaatcccg ctcgaattca gccatgctac ctaatgagac attgggctaa   1500
aaccgttttc tgtcgggatc tttagagagg gaaagcgttc aaatgagatg aattaagtat   1560
ttatgtttct caacaatctc ctttaagaac tttaaacatt taattttcac tcaagcaatc   1620
atgaaagttt tgtggggcta aggctcatct ggttgatttg gggtattgag agaattttgg   1680
tgagggaata gggtcattaa tagttgattg atataaactt gcccgacaac tggtgttttt   1740
tcgcccgatt ctagggattc ctttgattct ggaaccgtcg gcatcacttc ggtgtttggt   1800
gtttcagttg gaggggatcc tgcttctggt ggggctgga cattgggacg attgctgctg   1860
ctagtgggcg atcgccctgg tggcgaaaag gttgtggcag tctggttagt tgtatcttct   1920
gcctgccaag gatcgagggg ttgggttgtc gattgattcg cgggttttgg cggttgagtc   1980
tggtaagaag cggtggtttc ttggcgggac ggatcgccga tgaggctttg gggcgggaga   2040
attgcggcgg cggcgatcgc cgcttgaaat agggtagagc cataacctaa gcaggcattt   2100
tctcccactg agcattggcc aatgatcagg cagcctgccc cgataatcgc gccggcatgg   2160
atctcgatgt tgccgccgtg ggcctggata atcgcacctg caccaataca agcaccagtg   2220
gcgatcgcca cataattgcc ttcggttgct tgcagaataa caccgggggc aataaccgca   2280
cggggatgaa tccttacatc gccactaatt tgaatatctg gatgggtaat tgcctggaaa   2340
gtcacaatga ttctgtcaac ggtgattcaa ttaatcacag gtggggtaag ggttggggga   2400
tagacattcg ttttctcccc cataacgaag tggtcgcgtt acacaaccta ggggcgttgg   2460
ataatttcct caagcacccg tcgtttagcc gcttcatcga caccaatcat gcggacatat   2520
tcgccactgt gctcctggag acaaccttcg aggtgacgta aaacttctgc ctcttgggtg   2580
ctgtcaatgg tgccacaact actccaggac ttaacacgga aacggcgctt atcggcgtgt   2640
tctgttccaa tcttgtagcc ttgcatcaaa agcgaacgga ctttagaaac cacatcccca   2700
ctgagactcc cgctactgtg accccgaaa ccattgctgc ttggggctgc tttcgtgcct   2760
cccgaaaaac tactggttgc ggttgctgtc tggacaggcg cattgttgcc agggcgttgg   2820
atgatgatct ctgcggcccg tgttttggag ttggggtcaa cggcgattaa ctggacatat   2880
tcgttgggga actgggcggc gatcgcctgg atatttgcca aaatctgatt agcagaatga   2940
ccctccacaa agcctgcccc tagccaagac tgggttttaa aacggcgagt gctggcgtgt   3000
t                                                                  3001
```

<210> SEQ ID NO 7
<211> LENGTH: 792

```
<212> TYPE: DNA
<213> ORGANISM: Escherichia coli
<220> FEATURE:
<221> NAME/KEY: misc_feature
<222> LOCATION: (1)..(792)
<223> OTHER INFORMATION: aadA gene sequence

<400> SEQUENCE: 7
atgagggaag cggtgatcgc cgaagtatcg actcaactat cagaggtagt tggcgtcatc      60
gagcgccatc tcgaaccgac gttgctggcc gtacatttgt acggctccgc agtggatggc     120
ggcctgaagc cacacagtga tattgatttg ctggttacgg tgaccgtaag gcttgatgaa     180
acaacgcggc gagctttgat caacgacctt ttggaaactt cggcttcccc tggagagagc     240
gagattctcc gcgctgtaga agtcaccatt gttgtgcacg acgacatcat tccgtggcgt     300
tatccagcta agcgcgaact gcaatttgga gaatggcagc gcaatgacat tcttgcaggt     360
atcttcgagc cagccacgat cgacattgat ctggctatct tgctgacaaa agcaagagaa     420
catagcgttg ccttggtagg tccagcggcg gaggaactct ttgatccggt tcctgaacag     480
gatctatttg aggcgctaaa tgaaacctta acgctatgga actcgccgcc cgactgggct     540
ggcgatgagc gaaatgtagt gcttacgttg tcccgcattt ggtacagcgc agtaaccggc     600
agaatcgcgc cgaaggatgt cgctgccgac tgggcaatgg agcgcctgcc ggcccagtat     660
cagcccgtca tacttgaagc tagacaggct tatcttggac aagaagaaga tcgcttggcc     720
tcgcgcgcag atcagttgga agaatttgtt cactacgtga aaggcgagat caccaaggta     780
gtcggcaaat aa                                                        792

<210> SEQ ID NO 8
<211> LENGTH: 1935
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(1836)
<223> OTHER INFORMATION: FBP/SBPase-3HA gene sequence (From
      Synechococcus PCC7942, synthesized according to Chlamydomonas r.
      codon usage
<220> FEATURE:
<221> NAME/KEY: misc_feature
<222> LOCATION: (1837)..(1935)
<223> OTHER INFORMATION: 3 x HA tag

<400> SEQUENCE: 8
atggccgccg tcattgccaa gtcctccgtc tccgcggccg tgcccgccc ggcccgctcc       60 agcgtgcgcc ccatggccgc gctgaagccc gccgtcaagg ccgcccccgt ggctgccccg    120
gctcaggcca accagatgga gaagactatt ggcctggaga tcattgaggt ggtggagcag    180
gccgcgatcg cctccgctcg cctcatgggc aagggcgaga gaacgaggc tgaccgcgtg     240 gccgtggagg cgatgcgggt gcgcatgaac caggtggaga tgctgggccg catcgtgatt    300
ggcgagggcg agcgcgacga ggcgcccatg ctgtatatcg gcgaggaggt gggcatctac    360
cgcgacgcgg acaagcgcgc gggtgtgccc ccggcaagc tggtggagat cgacattgcc     420 gtggaccct gcgagggcac caacctgtgc gcgtacggcc agccgggtc catggccgtc      480 ctggccatca gcgagaaggg cggcctgttc gcggcccccg acttctacat gaagaagctg    540
gcggctcctc cggcggcgaa gggcaaggtc gacattaaca gtcggccac ggagaacctg     600 aagatcctgt ccgagtgcct ggaccgggcc atcgatgagc tggtggtggt cgtgatggac    660
atggccgccg tcattgccaa gtcctccgtc tccgcggccg tgcccgccc ggcccgctcc    720
```

```
agcgtgcgcc ccatggccgc gctgaagccc gccgtcaagg ccgcccccgt ggctgccccg       780
gctcaggcca accagatgga gaagactatt ggcctggaga tcattgaggt ggtggagcag       840
gccgcgatcg cctccgctcg cctcatgggc aagggcgaga agaacgaggc tgaccgcgtg       900
gccgtggagg cgatgcgggt gcgcatgaac caggtggaga tgctgggccg catcgtgatt       960
ggcgagggcg agcgcgacga ggcgcccatg ctgtatatcg gcgaggaggt gggcatctac      1020
cgcgacgcgg acaagcgcgc gggtgtgccc gccggcaagc tggtggagat cgacattgcc      1080
gtggacccct gcgagggcac caacctgtgc gcgtacggcc agccggggtc catggccgtc      1140
ctggccatca gcgagaaggg cggcctgttc gcggcccccg acttctacat gaagaagctg      1200
gcggctcctc cggcggcgaa gggcaaggtc gacattaaca agtcggccac ggagaacctg      1260
aagatcctgt ccgagtgcct ggaccgggcc atcgatgagc tggtggtggt cgtgatggac      1320
cggccgcgcc acaaggagct catccaagag atccgccagg cgggtgcccg ggtgcgcctg      1380
atcagcgacg gggacgtgag cgcggctatc agctgcggct cgcggggac caacacccac       1440 gccctgatgg gcatcggcgc cgctcctgag ggcgtgatta gcgccgcggc gatgcgctgc      1500
ctgggcggcc actttcaggg ccagctgatc tacgacccgg aggtggtgaa gacgggcctc      1560
atcggcgagt cgcgcgagtc gaacatcgcc cggctgcagg agatggggat cacggacccc      1620
gaccgcgtgt acgatgctaa cgagctggct tcgggccagg aggtcctctt cgccgcctgc      1680
ggcatcaccc ccggcctgct gatggagggc gtccgcttct tcaagggtgg cgcccggacc      1740
cagagcctcg tcatttcctc gcagtcgcgc acggcccgct tcgtggacac cgtccacatg      1800
ttcgacgacg tgaagaccgt gagcctgcgc ctggagtacc cctacgacgt gccggactac      1860
gcgggctacc cttacgacgt ccccgattat gccggttcct acccgtacga tgtgcccgac      1920
tacgccgccc agtaa                                                        1935
```